US009943658B2

(12) United States Patent
Baker

(10) Patent No.: US 9,943,658 B2
(45) Date of Patent: Apr. 17, 2018

(54) CPAP MASK SKIN ADHESIVE APPLICATOR

(71) Applicant: Melinda Baker, Massillon, OH (US)

(72) Inventor: Melinda Baker, Massillon, OH (US)

( * ) Notice: Subject to any disclaimer, the term of this patent is extended or adjusted under 35 U.S.C. 154(b) by 604 days.

(21) Appl. No.: 14/185,515

(22) Filed: Feb. 20, 2014

(65) Prior Publication Data
US 2014/0238403 A1 Aug. 28, 2014

Related U.S. Application Data

(60) Provisional application No. 61/770,075, filed on Feb. 27, 2013.

(51) Int. Cl.
*A61M 16/06* (2006.01)

(52) U.S. Cl.
CPC ..... *A61M 16/0605* (2014.02); *A61M 16/0633* (2014.02); *A61M 16/0683* (2013.01); *A61M 2205/0238* (2013.01); *A61M 2209/04* (2013.01)

(58) Field of Classification Search
CPC .. A61M 16/0605; B43M 11/02; B43M 11/06; B43M 11/085; B05C 1/006; B43K 7/005; B43K 23/004
USPC ............................................ 401/11, 193, 209
See application file for complete search history.

(56) References Cited

U.S. PATENT DOCUMENTS

| 564,178 | A | * | 7/1896 | Ahrens | B43K 23/004 15/443 |
| 2,095,650 | A | * | 10/1937 | Reichenbach | A24F 25/00 401/11 |
| 2,496,086 | A | * | 1/1950 | Fitzgerald | B43K 23/004 15/428 |
| 2,930,061 | A | * | 3/1960 | O'Neil | B05C 17/00516 401/11 |
| 3,523,628 | A | * | 8/1970 | Colvin | B43K 1/086 401/213 |
| 4,932,565 | A | * | 6/1990 | Paradiso | B05C 17/00516 222/174 |
| 4,940,350 | A | * | 7/1990 | Kim | B43M 11/085 401/209 |
| 5,810,495 | A | * | 9/1998 | McAuley | A45D 34/041 401/213 |
| 5,984,557 | A | * | 11/1999 | Fennell | B05C 17/00516 401/193 |
| 6,341,606 | B1 | | 6/2002 | Bordewick | |

(Continued)

*Primary Examiner* — Jennifer C Chiang
*Assistant Examiner* — Bradley Oliver
(74) *Attorney, Agent, or Firm* — Global Intellectual Property Agency, LLC; Jordan Sworen

(57) ABSTRACT

Provided is an applicator device for facilitating the application of liquid adhesive onto the edge of a continued positive air pressure (CPAP) mask. The device has a central shaft with a hollow interior. One of the central shaft removably secures to a storage container of skin safe adhesive. The opposing end includes two arcuate guide arms extending upwardly to form a concave inner surface adapted to accept the edge of a CPAP mask. Within the central shaft and protruding outward from the upper opening is a liquid adhesive roller ball. The ball is the primary application surface for conveying adhesive onto the CPAP mask edge. In use the applicator is secured to the opening of an adhesive storage container and the assembly is then inverted onto the edge of a CPAP mask to apply liquid adhesive thereto, improving the seal between the mask edge and a user's face when deployed.

11 Claims, 2 Drawing Sheets

(56) References Cited

U.S. PATENT DOCUMENTS

| | | |
|---|---|---|
| 8,318,859 B2 | 11/2012 | Amano |
| 2004/0169053 A1* | 9/2004 | Liljeqvist .......... B05C 17/00516 |
| | | 222/611.1 |
| 2005/0284479 A1 | 12/2005 | Schader |
| 2007/0127978 A1* | 6/2007 | Park ........................ A46B 3/04 |
| | | 401/193 |
| 2012/0006329 A1 | 1/2012 | Beevers |
| 2013/0121746 A1* | 5/2013 | Brindise, Jr. ........ B43K 23/016 |
| | | 401/6 |

* cited by examiner

CPAP MASK SKIN ADHESIVE APPLICATOR

CROSS REFERENCE TO RELATED APPLICATION

This application claims the benefit of U.S. Provisional Application No. 61/770,075 filed on Feb. 27, 2013. The above-identified patent application is herein incorporated by reference in its entirety to provide continuity of disclosure.

BACKGROUND OF THE INVENTION

Field of the Invention

The present invention relates to biomedical device accessories. More specifically, it relates an applicator for skin adhesive. The skin adhesive is applied, via the applicator to the exterior of a biomedical device that requires regular contact with a user's skin. Once a layer of adhesive is applied to the exterior of the biomedical device, it can be safely secured to the patient's skin for a limited duration of time. The applicator is especially well suited to the task of applying adhesive to breathing masks.

Continuous positive airway pressure (CPAP) is a form of respiratory treatment involving the steady flow if forced air into a patient's respiratory passages. The treatment is used to aid patients suffering from a number of respiratory disorders such as sleep apnea, collapsed airways, respiratory infection, and certain neuromuscular conditions. By continuously forcing air into the patient's lungs, the CPAP machine helps prevent airways from collapsing and ensures that patients receive adequate air intake with each breath.

In most units is air stream is generated by a propeller within a base station and pushed through a tube connected to a facemask. This face mask is placed over the patient's nose and mouth and snuggly fitted to the skin, in order to trap air within the quarantined area and enable same to enter the patient's nose and mouth. Proper function of the device requires that the mask be firmly seated on the patient's face, otherwise air may leak out of the spaces between the mask and the patient's face.

To keep CPAP masks firmly seated in the proper position, healthcare professionals have developed several securing methods. Some masks come with elaborate harness structures that encircle the user's head in multiple directions. The harness restricts movement of the mask, but may also encumber the patient's normal head movement. Other methods include the application of adhesive tape to the mask edges. The tape is firmly pressed to the mask and then the mask is pressed down onto the user's skin. Variations on this method include masks that come with adhesive pre-applied to the mask edge. These adhesion methods require that the mask be discarded once the adhesive material has worn off, thus making them an expensive option for every day use.

A CPAP mask securing method is needed that does not result in the constriction of the wearer's head movements and does not require frequent discarding of masks. The present invention provides an adhesive applicator for applying skin safe adhesive to the edges of a CPAP mask. In this manner, the invention provides patients with an inexpensive and easy to use means of securing a mask to their face.

Description of the Prior Art

Devices have been disclosed in the prior art that relate to adhesive applicators. These include devices that have been patented and published in patent application publications. These devices generally relate to adhesive applicators with convex application structures. The following is a list of devices deemed most relevant to the present disclosure, which are herein described for the purposes of highlighting and differentiating the unique aspects of the present invention, and further highlighting the drawbacks existing in the prior art.

One method of adhering a CPAP mask to patient's face involves the application of double-sided tape. The tape is coated on one or both sides with a skin adhesive and on at least one side with a plastic suitable adhesive. In Beevers, US Patent Application Publication No. 2012/0006329, a piece of U-shaped double-sided tape is disclosed. The tape is placed over the bridge of the nose and long opposing sides, near the joint of the nose and the face. A CPAP mask is then placed in position over the nose and mouth then pressed downwards to form a seal between the mask and exposed portion of the u-shaped tape. This method is problematic because any dirt and debris that accumulate on the tape can reduce effectiveness of the invention. The present invention solves this problem by providing an applicator for applying liquid adhesive directly to the CPAP mask.

Some CPAP masks directly integrate the adhesive into the mask. By way of example, Schrader, US Patent Application Publication No. 2005/0284479 teaches a CPAP mask with a seal around the interior perimeter of the mask. This seal is coated in an adhesive substance that bonds gently to a patient's skin. The mask can be easily removed via the application of retrograde force. The problem with such masks is that they must be replaced after the adhesive wears off, making their use expensive and impractical for many patients. The present invention facilitates reuse of the same CPAP mask with renewed application of adhesive from the applicator.

Disposable masks having adhesive bonding around the perimeter were created to address the problem involved with cost of adhesive masks. Bordewick, U.S. Pat. No. 6,341,606 teaches a facemask that covers the nose and has a triangular formation of adhesive bonding around the perimeter. Respiratory tubing can be secured to the mask through an opening. After the mask is used, it is discarded. Though these masks may be made of cheaper materials, they do not resolve the cost associated with the frequent purchase of new masks. The present invention does not require users to frequently purchase new supplies because the same CPAP mask can be continuously used so long as adhesive fluid is available for the applicator.

Pressure sensitive adhesives are known in the art of adhesion and have found many applications since their conception. Amano, U.S. Pat. No. 8,318,859 teaches a pressure-sensitive adhesive. The adhesive is applied to two distinct objects, which are then pressed together to form a bond. Retrograde force may be sufficient to break the seal depending upon the strength of the force applied.

These prior art devices have several known drawbacks. They do not provide a system for reapplying adhesive to a facemask, so that the mask may be reused. The present invention provides an applicator for dispersing adhesive onto a CAP mask, thereby facilitating securement of the mask. Adhesive may be continuously reapplied using the applicator of the present invention. It substantially diverges in design elements from the prior art and consequently it is clear that there is a need in the art for an improvement to existing mask-retention devices. In this regard the instant invention substantially fulfills these needs.

SUMMARY OF THE INVENTION

In view of the foregoing disadvantages inherent in the known types of CPAP mask securing means now present in the prior art, the present invention provides a new adhesive applicator wherein the same can be utilized for providing convenience for the user when applying adhesive to a CPAP mask.

The invention is an applicator tip that removably secures to the opening of an adhesive storage bottle. The applicator tip comprises a central shaft with a hollow interior region, a pair of guide arms extending from an upper end of the shaft, a roller ball trapped within the junction of the shaft opening and the guide arms, and a support ridge extending around the exterior of the central shaft. One end of the central shaft is open to receive the opening of an adhesive storage container such as a bottle of skin glue. Optionally, there may be threading, ridges, or nubs along the interior wall(s) of the central shaft to aid in securement to an adhesive storage container.

When the applicator tip is secured to the opening of an adhesive storage container, the tip becomes a dispensing nozzle designed to accommodate CPAP masks. The two guide arms have concave interior surfaces and convex outer surfaces. These arms form a u-shaped cross-section and can hug the sides of a CPAP mask edge as adhesive is applied. A roller ball is trapped within the opening of the central shaft proximal to the guide arms. The ball blocks the flow of adhesive through the central shaft to prevent adhesive from pouring out of the opening between the guide arms, and also acts as the primary applicator surface. As the roller ball is rolled along the edge of the CPAP mask, the portion of the ball on the interior of the central shaft is coated in adhesive and rolled until it becomes exposed through the opening between the guide arms. In this manner, adhesive is distributed along the edge of the mask.

The ability to apply adhesive as needed enables the use of any CPAP mask rather than a disposable or pre-treated mask. Patients or nurses can select the mask of their choice, attach the applicator tip to a bottle of skin adhesive, and then apply the adhesive to the mask. This procedure can be repeated daily or as needed, without necessitating a change in masks. Thus, patients are able to save money on medical supplies through efficient re-use of masks.

It is therefore an object of the present invention to provide a new and improved adhesive applicator device that has all of the advantages of the prior art and none of the disadvantages.

It is another object of the present invention to provide a means for applying adhesive to any CPAP mask as needed.

Another object of the present invention is to provide an applicator tip that secures to an adhesive storage container to enable dispensing of the adhesive onto a CPAP mask.

Yet another object of the present invention is to provide an applicator tip designed to conform to the edges of a CPAP mask, thereby reducing the level of fine motor function necessary to apply adhesive to the edge of a CPAP mask.

Still another object of the present invention is to provide a portable applicator that can be used anywhere and anytime a CPAP mask is needed.

A further object of the present invention is to provide an applicator tip that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
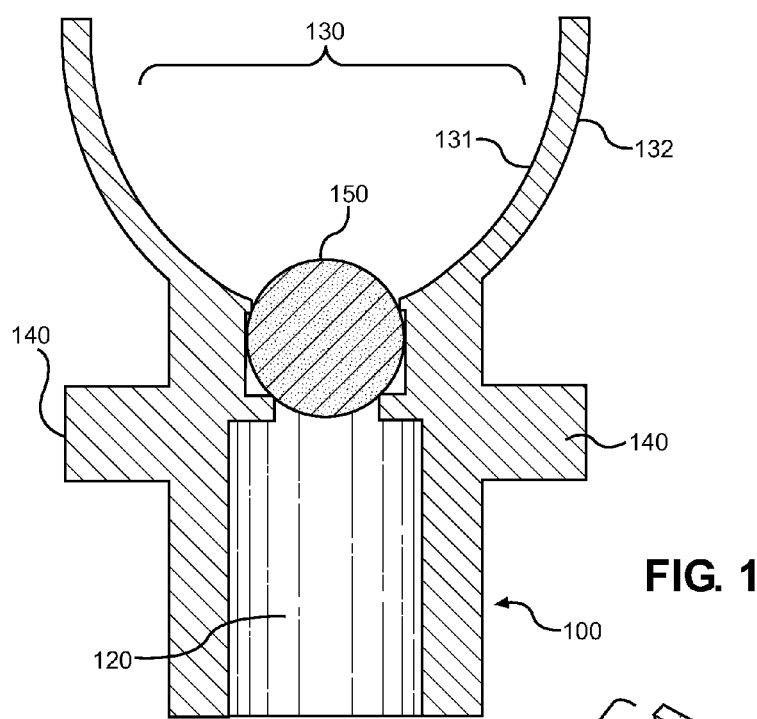
FIG. 1 shows a cross-section view of the applicator tip of the present invention.

Reference is made herein to the attached drawings. Like reference numerals are used throughout the drawings to depict like or similar elements of the adhesive applicator tip. For the purposes of presenting a brief and clear description of the present invention, the preferred embodiment will be discussed as used for applying adhesive to the edge of a CPAP mask. The figures are intended for representative purposes only and should not be considered to be limiting in any respect.

Referring now to FIG. 1, there is shown a cross-section of the applicator device. The applicator device 100 has a central shaft 120 with a hollow interior that may have uniform diameter throughout, or may be stepped (as shown), contoured, or tapered in order to control flow of liquid therethrough. Although, the hollow interior region may vary in diameter according to manufacturing needs, it should be sized to accommodate the opening of a bottle of adhesive. Threading, nubs, or other retention means may be disposed along the wall(s) of the hollow interior region in order to facilitate removable securement of the applicator device to the container of adhesive. The retention means is disposed along second end of central shaft and comprises a means to secure the same to a liquid adhesive container during application of the adhesive to the CPAP mask prior to mask use.

A pair of guide arms 130 convexly extends outward from the end of the central shaft distal from an adhesive bottle connection end. Each guide arm has an arcuate shape with a concave inner surface 131 and convex outer surface 132. These arms extend from the central shaft 120 in an outward and upward curve, and do not obscure the opening into the hollow interior region. At their uppermost edges, the guide arms should be substantially mirrored in shape with respect to one another so as to enable the applicator to hug the sides of a CPAP mask edges. The length of each arm is preferably equal to or grater than the exterior diameter of the central shaft.

Trapped within the hollow interior is a spherical roller ball 150 that is capable of free rotation in place. In a preferred embodiment, the central shaft opening lying between the guide arms 130. The opening should have a diameter less than that of the equatorial diameter of the sphere to prevent it from dislodging. A small lip extending centrally inward or upward from the upper edge of the hollow interior may optionally be included to effectively reduce the diameter of the opening. Further, there may be a portion of the hollow interior having a region of reduced diameter to prevent the roller ball from dropping out the bottom of the interior region. When the device is in use, adhesive fluid flows into and through the hollow interior region of the central shaft, coating the interiorly directed portion of the roller ball 150. The ball is moved across the surface of a CPAP mask edge, causing the interiorly directed surface area of the ball to roll towards the outside, thereby brings the liquid adhesive into contact with the CPAP mask edge. The roller ball 150 effectively communicates the liquid adhesive from the interior 120 to the exposed portion of the roller ball 150 when the ball is rolled in place. When pressed against a CPAP mask edge, the roller ball 150 makes contact therewith to apply a thin film of adhesive via contact exchange.

One or more support shelves 140 protrude outward from the exterior of the central shaft. This shelf may be a single protrusion encircling the central shaft 120 or may be discrete sections lying within the same planar space along the shaft exterior. The purpose of the support shelf is to provide a place for the fingers to rest when the applicator device is in use. During use the applicator and connected adhesive storage container may be inverted to promote flow of adhesive into the applicator's hollow interior region. Presence of a support shelf prevents the user from having to grip the central shaft or convex guide arms for support. Instead, the fingers are rested upon the support shelf, where they can exert gentle downward pressure to maintain steady contact between the roller ball and the CPAP mask edge.

Figure 2:
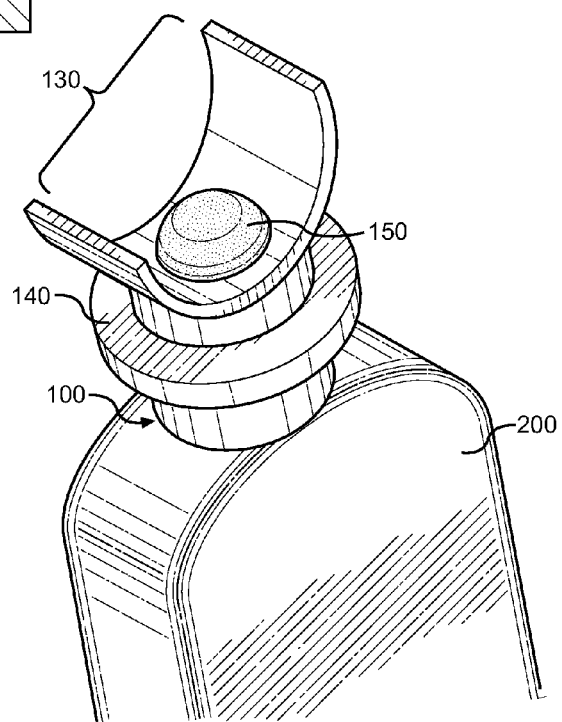
FIG. 2 shows a perspective view of the applicator tip connected to an adhesive storage container.

Turning now to FIG. 2, the applicator device is shown attached to the opening of an adhesive storage container. The open end of the central shaft 120 sits upon a protruding opening of the storage bottle. Guide arms 130 extend arcuately upward from the end of the central shaft opposite the storage container. The roller ball 150 pokes out through the upper opening of the central shaft. A small lip around the upper opening prevents the ball from dislodging from the hollow interior while in use. Along the exterior of the central shaft a support shelf 130 protrudes to facilitate finger placement.

Figure 3:
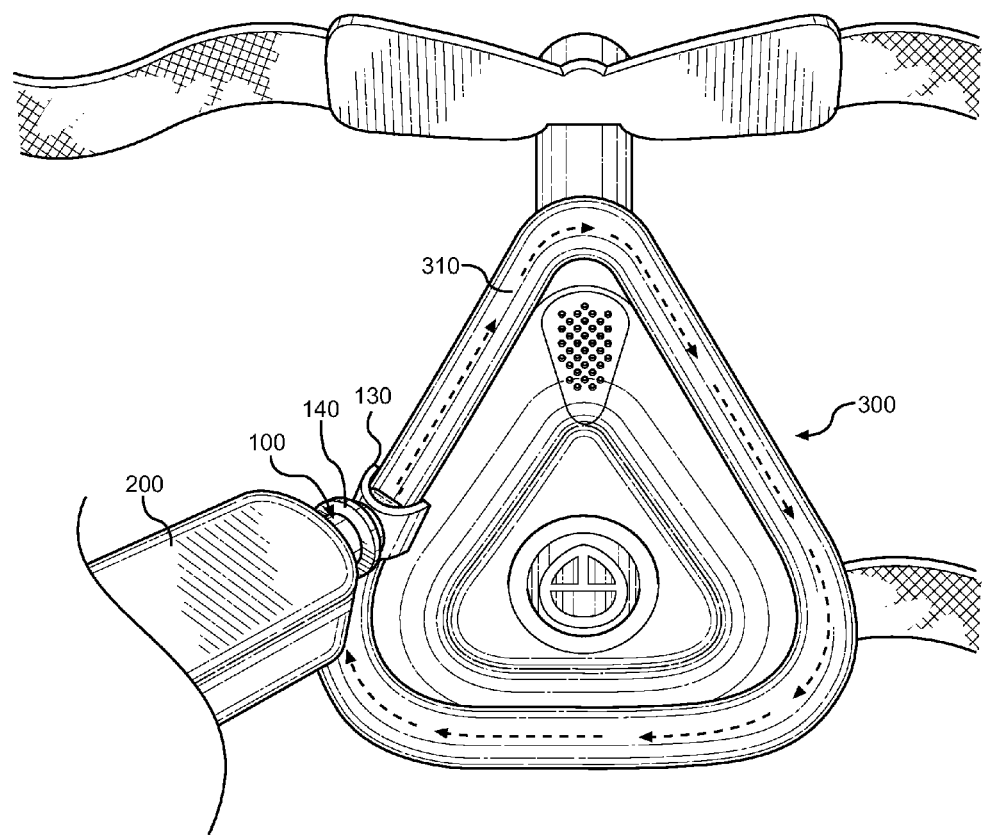
FIG. 3 shows a perspective view of the applicator tip in use for applying adhesive to the edge of a CPAP mask.

An illustration of the applicator device in use is shown in FIG. 3. A CPAP mask 300 lies with it's facial opening directed upwards and the mask edge 310 exposed. The applicator device 100 attached to an adhesive storage container 200 is inverted over the mask edge. Guide arms 130 are positioned over the sides of the mask edge such that the roller ball is centrally disposed along the apex of the mask edge. The adhesive coated roller ball is then moved along the mask edge until the entire length is well coated in adhesive. A user can rest their fingers upon the support shelf 140 and exert downward pressure there upon to keep the device properly inverted and positioned. Maintained inversion of the adhesive container throughout application is important to ensure proper flow of liquid adhesive through the hollow interior of the central shaft and onto the roller ball surface. Once the mask edge is coated, the applicator device and bottle may be placed in an upright position, the applicator tip removed and cleaned, and the adhesive storage container sealed for later use.

The present invention is an adhesive applicator specially designed to accommodate and hug the contours of a CPAP mask edge. The guide arms and roller ball applicator enable the controlled, even application of liquid adhesive along a CPAP mask edge without requiring significant finger dexterity. The guide arms prevent the applicator from slipping off the mask edge, making it easy for a user to slide the applicator in a forward or backward direction.

The roller ball may be constructed of metal, plastic, or alternatively may be made of a sponge like material. Solid non-porous embodiments are desired in situations where the applicator will be removed from the adhesive bottle and cleaned after each use. Conversely, the sponge material may be desirous in situations where the applicator is constantly connected to an adhesive storage container that is in frequent use. In either embodiment, the roller ball should be spherical in shape.

The specific shape and size of the device may vary according to the type of adhesive storage container is must fit. Embodiments illustrated herein are limited to cylindrical central shafts, but the device may employ shafts of any particular cross-sectional geometry. Similarly, the material construction of the device may vary as needed.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A liquid adhesive applicator device removably securable to a liquid adhesive storage container, comprising:
   a central shaft including a hollow interior region extending from an upper opening disposed on a first end of the central shaft to a lower opening disposed on a second end of the central shaft;
   a roller ball rotatably disposed between the upper opening and an interior portion of the hollow interior region of the central shaft;
   wherein the upper opening includes a diameter less than a diameter of the equatorial diameter of the roller ball, such that the roller ball is prevented from falling out of the upper opening;
   wherein the interior portion includes a diameter less than the diameter of the equatorial diameter of the roller ball, such that the roller ball is prevented from falling out of the lower opening;
   wherein a portion of the roller ball protrudes outwardly from the upper opening;
   a pair of arcuate guide arms disposed at the first end of the central shaft, each of the pair of arcuate guide arms including a length protruding radially outwardly relative to a longitudinal axis of the central shaft, each of the pair of guide arms including an exterior surface having a convex shape relative to the longitudinal axis of the central shaft and an interior surface having a concave shape relative to the longitudinal axis of the central shaft;
   a support shelf disposed between the upper opening and the lower opening of the central shaft, the support shelf extending annularly around an exterior surface of the central shaft;
   wherein the support shelf is configured such that a user can rest their fingers upon the support shelf and exert downward pressure there upon.

2. The liquid adhesive applicator device of claim 1, wherein said hollow interior region is wider near said lower opening than it is near said upper opening, so as to receive the opening of a liquid adhesive storage container when in use.

3. The liquid adhesive applicator device of claim 1, wherein a securing means is disposed along said hollow interior region near said lower opening, so as to removable secure said central shaft to a liquid adhesive container when in use.

4. The liquid adhesive applicator device of claim 1, wherein said curvature of said guide arms is greatest near said first end of said central shaft and diminishes towards the top of said guide arms.

5. The liquid adhesive applicator device of claim 1, wherein said roller ball is constructed of a non-porous material.

6. The liquid adhesive applicator device of claim 1, wherein said roller ball is constructed of a porous material.

7. The liquid adhesive applicator device of claim 1, wherein said second end of central shaft may further comprise a liquid adhesive container retention means thereon.

8. The liquid adhesive applicator device of claim 1, wherein the pair or arcuate guide arms mirror one another, such that they form an arcuate cavity therebetween, the arcuate cavity including a diameter larger than a diameter of the central shaft, but smaller than a diameter of the support shelf.

9. The liquid adhesive applicator device of claim 1, wherein the support shelf comprises a planar disc member protruding perpendicularly outwardly relative to the longitudinal axis of the central shaft.

10. The liquid adhesive applicator device of claim 1, wherein the upper opening includes a lip extending radially inwardly from a perimeter edge of the upper opening for decreasing the diameter of the upper opening.

11. The liquid adhesive applicator device of claim 10, wherein the interior portion of the hollow interior region includes an interior shoulder extending radially inwardly for decreasing a diameter of the interior portion.

* * * * *